United States Patent [19]

Luderer et al.

[11] 4,282,315

[45] Aug. 4, 1981

[54] PREPARATION OF ENRICHED WHOLE VIRUS RADIOLIGAND

[75] Inventors: Albert A. Luderer, Corning; Hugh C. McDonald, Horseheads, both of N.Y.

[73] Assignee: Corning Glass Works, Corning, N.Y.

[21] Appl. No.: 74,918

[22] Filed: Sep. 13, 1979

[51] Int. Cl.[3] .......................... C12N 7/00; C12N 7/02; G01N 33/54; G01N 33/00

[52] U.S. Cl. .......................................... 435/5; 435/7; 435/177; 435/188; 435/235; 435/236; 435/239; 424/1.5; 424/12; 23/230 B

[58] Field of Search ............... 23/230 B, 230.3; 424/1, 424/1.5, 8, 12, 89; 435/4, 5, 7, 235, 236, 810, 239, 188, 177

[56] References Cited

U.S. PATENT DOCUMENTS

| | | | |
|---|---|---|---|
| 3,826,613 | 7/1974 | Parikh et al. | 435/5 |
| 4,168,300 | 9/1979 | Andersson et al. | 424/89 |
| 4,176,174 | 11/1979 | Russell et al. | 424/89 |
| 4,178,360 | 12/1979 | Cleeland et al. | 424/12 |
| 4,195,074 | 3/1980 | Safford | 424/89 |

OTHER PUBLICATIONS

McDonald et al., "Preparation and Characterization of an $^{125}$T-Labeled Sendai Virus Ligand", *Anal. Biochem.* vol. 106, (1980), pp. 127-133.

Baird et al., "Evidence That MuLV-Induced Thymic Lymphoma Cells Possess Specific Cell Membrane Binding Sites For MuLV", *Int. J. Cancer,* vol. 19, (1977), pp. 403-413.

Fowler et al., "Binding Characteristics of Rauscher Leukemia Virus Envelope Glycoprotein gp 71 to Murine Lymphoid Cells", *J. Vir.* vol. 24, No. 3 (1977), pp. 729-735.

Greaves, "Virus 'Receptors' on Lymphocytes", *Scand. J. Immunol.*, vol. 5, Suppl. 5, (1976), pp. 113-123.

Scheid et al., "Activation of Cell Fusion and Infectivity by Proteolytic Cleavage of a Sendai Virus Glycoprotein", *Proteuses and Biological Control,* Cold Spring Harbor Laboratory, (1975), pp. 645-659.

Shuurs et al., "Enzyme-Immunoassay", *Clin. Chim. Acta,* vol. 81, No. 1 (1977), pp. 1-40.

Fenner et al., *Medical Virology,* Academic Press, NY, (1970), pp. 45-46.

Baum et al., "Affinity Chromatography", *Immobilized Enzymes, Antigens, Antibodies, and Peptides,* Weetall ed., Marcel Dekker, Inc., NY, pp. 419-425, 451-454.

*Primary Examiner*—Thomas G. Wiseman
*Attorney, Agent, or Firm*—William E. Maycock

[57] ABSTRACT

Obtaining a virus subpopulation, useful in qualitative and quantitative biological assay procedures, of enhanced sensitivity toward host cells for the virus by contacting a virus population with an inanimate substrate having moieties which mimic host cell receptor sites for cell binding protein of the virus and recovering as said subpopulation the portion of the initial virus population which complexes with the substrate.

42 Claims, 2 Drawing Figures

PREPARATION OF ENRICHED WHOLE VIRUS RADIOLIGAND

BACKGROUND OF THE INVENTION

Baird et al., *Int. J. Cancer*, 19, 403–417 (1977), have reported on binding assays of a radioviral ligand prepared from whole murine leukemogenic virus with mouse thymus lymphoma cells. The percent binding of the radioligand to presumptively receptor positive cells was low ($\cong 10\%$) and the amount of radioligand added to obtain significant uptake was high ($>100,000$ cpm). This type of result obtained in a whole virus radioligand-receptor cell binding study is quite different from that in the use of radiolabeled virus in radioimmunoassay procedures based on antigencity, where ligand binding activity or sensitivity is generally higher.

Similar to the whole virus cell receptor study, Fowler et al., *J. Virol.*, 24, 729–735 (1977), have reported studies using radiolabeled surface glycoprotein of murine leukemia virus as a cell binding ligand. Only a portion (15–40%) of the antigenically competent radiolabeled glycoprotein was bound to susceptible murine cell lines.

The above indicates an inability to prepare an effective cell binding radioviral ligand which would not only be a useful antigenic substance but could also be used to quality and quantify cell receptors.

SUMMARY OF THE INVENTION

It is an object of this invention to provide virus whole cell subpopulations which, after labeling for ease of identification and measurement, can be used as an effective tool to probe cell membrane receptors.

Another object of this invention is to provide a process for preparing virus whole cell subpopulations which, after labeling for ease of identification and measurement, can be used as an effective tool to probe cell membrane receptors.

A further object of this invention is to provide virus whole cell subpopulations useful as antigenic substances in conventional complementary (i.e., selective binding) procedures, such as immunoassay techniques.

In specific embodiments, it is an object of this invention to provide virus whole cell subpopulations which will bind preferentially with the type of sialic acid receptor, typically N- or O-acetylneuraminic acid, found in human and sheep red blood cells and in many mammalian white blood cells.

A preferred object of this invention is to provide influenza and paramyxovirus subpopulations, or other virus subpopulations which bind to sialic acid-containing surface proteins, most preferably Sendai virus subpopulations, which can be labeled and then used to effectively probe cell receptors of the sialic acid type.

Other objects of the invention will be apparent to the skilled artisan.

It has now been found that an enriched viral subpopulation characterized by good sensitivity toward complementary cell receptors can be prepared through the use of protein, preferably immobilized, or cells or cell derivatives having receptor sites complementary to the binding protein(s) of the cell membrane which normally participates in the reaction with virus. More specifically, viruses are brought into contact with an immobilized substrate, to which the virus can be complexed and then released. While the complex is in existence, it is washed to remove non-complexed material. Although the non-complexed material may have excellent antigenic properties, it has been found that the cell receptor binding activity is substantially contained within the complexed portion.

Various methods, depending upon particular virus and substrate, can be used to effect the complexation-release steps. For example, acid, base, temperature and the like, alone or in combination, may prove useful in a given situation.

Preferably, the enriched virus subpopulation is converted to a radioligand using conventional procedures prior to use.

In a more specific embodiment, Sendai virus is enriched using an immobilized protein substrate having N-acetylneuraminic acid moieties such as fetuin. The complexation-release steps are temperature dependent, which provides a ready mode to prepare the enriched subpopulation and separate it from the unwanted particles. Conversion of the enriched Sendai virus to a radioligand provides an effective antigenic, as well as cell receptor, tool.

DESCRIPTION OF THE DRAWINGS

The figures of the drawings show a comparison of the gel profiles of iodinated whole Sendai virus purified biochemically (FIG. 1) and by adsorption and elution from immobilized fetuin (FIG. 2). Viral proteins are designated as (NP) nucleoprotein, (HN) hemagglutinin-neuraminidase, (F-1) fusion factor, and (M) membrane protein.

DETAILED DESCRIPTION OF THE INVENTION

Figure 1:
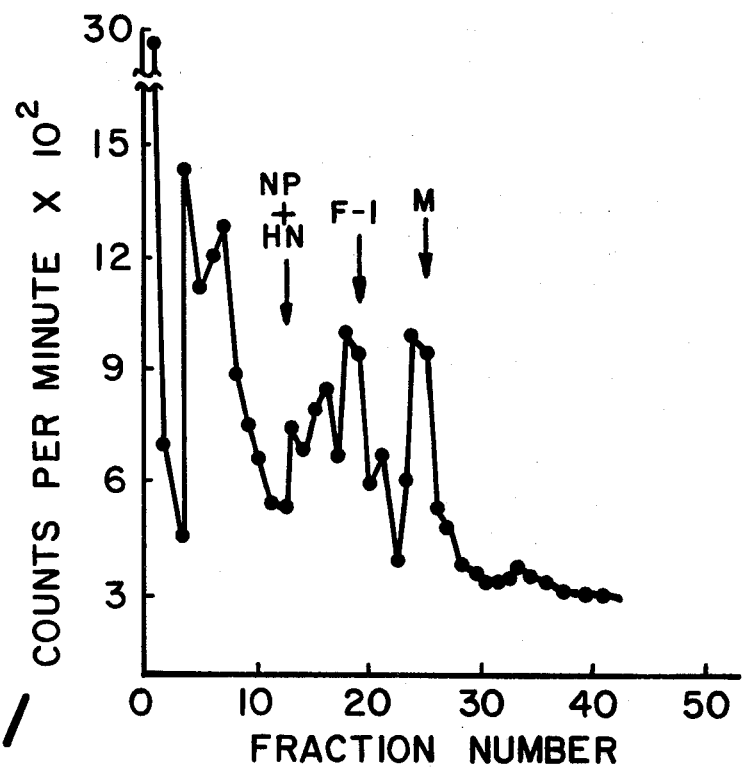

For a variety of reasons, there is increasing inquiry into the mechanisms involved in virus-host cell interactions. In addition to the area of infectious diseases caused by viruses, virus-cell interplay is of immense interest in general genetic studies, cell metabolism, immunology and so on. A receptivity toward certain types of viruses may indicate previous infection, susceptibility toward infection or the like. But in order to advance this growing area of research, effective viral tools are needed to qualitatively and quantitatively probe receptor-bearing cells.

Virus populations used in research laboratories are either cultured in the laboratory or purchased from a culturing source. Regardless, the viral population, although having high antigenic properties, in many cases has low sensitivity toward host cell receptors. This is illustrated by the following example.

EXAMPLE I

Ultraviolet light-inactivated Sendai virus obtained from Microbiological Associates of Walkersville, MD was biochemically purified by pelletization at $38,000 \times g$ for 90 minutes in an RC-2B Sorvall refrigerated centrifuge (Ivan Sorvall Co., Norwich, Conn.), or by Sepharose 4B chromatography. Gel filtration of the virus was carried out at 4° C. using a column ($50 \times 1$ cm) of Sepharose 4B (Pharmacia Fine Chemicals, Uppsala, Sweden) equilibrated with phosphate buffered saline, pH 7.3. Fractions were monitored by adsorption at 280 nm. Thereafter, labeling with $I^{125}$ was carried out by a standard chloramine-T or lactoperoxidase procedure with separation of unreacted $I^{125}$ by filtration through a Sepharose 4B column to yield the Sendai virus radioligand.

Where immobilized substrate was used, immobilization was carried out using an arylamine derivative of controlled pore glass. See Weetall, H. H., et al., *Methods in Enzymology*, 34B, Academic Press, New York (1974) (Jakoby and Wilchek, ed.).

The binding of the radioligand was determined using the following procedure: The binding of ligand to cells or immobilized antisera (IMA) was performed in RPMI 1640 (Grand Island Biochemical Co., Grand Island, N.Y.) plus 0.5% BSA (bovine serum albumin). Cells or IMA previously washed in buffer were added to plastic tubes (11 cm×1 cm). The samples were brought to a total volume of 0.9 ml with buffer and then 0.1 ml of ligand (previously diluted in buffer) containing 10,000 to 100,000 counts was added. The reaction was incubated at 4° C., and the tubes were centrifuged (2000×g, 10 minutes). After pouring off the supernatant fluid, the pellets were counted in a Packard Model 3000 Gamma Scintillation Spectrophotometer. The results are shown in Table I.

TABLE I

BINDING OF IODINATED BIOCHEMICALLY PURIFIED SENDAI VIRUS TO CELLS AND IMMOBILIZED ANTIBODY

| SAMPLE | AMOUNT | INCUBATION | % TOTAL COUNTS BOUND |
|---|---|---|---|
| Blank | — | 1 hr, 4° C. | 9.6% |
| SRBC | $10^8$ cells | 1 hr, 4° C. | 8.3% |
| SRBC | $10^7$ cells | 1 hr, 4° C. | 12.2% |
| Blank | — | 1 hr, 4° C. | 6.7% |
| CCL-119 | $2.5 \times 10^6$ cells | 1 hr, 4° C. | 7.4% |
| Blank | — | 16 hr, 4° C. | 6.7% |
| SRBC | $10^8$ cells | 16 hr, 4° C. | 11.5% |
| SRBC | $10^7$ cells | 16 hr, 4° C. | 8.8% |
| Blank | — | 1 hr, 4° C. | 10.0% |
| SV-IMA | 1.25 mg(glass) | 1 hr, 4° C. | 70.7% |
| NRS-IMA | 2.0 mg(glass) | 1 hr, 4° C. | 18.0% |

Abbreviations:
SRBC - sheep red blood cells.
CCL-119 - acute lymphoblastic leukemia (human) cell line.
SV-IMA - immobilized rabbit anti-Sendai virus on controlled-pore glass.
NRS-IMA - immobilized rabbit normal serum on controlled-pore glass.

Cell line CCL-119 was cultured at 36° C. in an atmosphere of 5% $CO_2$, maintained by serial passage in RPMI-1640 plus 20% fetal calf serum, supplemented with glutamine and gentamycin (Schering Corp., Kenilworth, N.J.). The cells were washed twice in assay buffer prior to resuspension for the binding studies.

Sheep red blood cells and CCL-119 are receptor positive for Sendai virus, but the virus population exhibits very little sensitivity toward the cell receptors. This is in accordance with earlier studies discussed in the background portion of this specification, hereinbefore. On the other hand, there is pronounced antigencity in the virus population as shown by binding to rabbit anti-Sendai virus serum in comparison with normal rabbit serum.

Although the above experiment uses only a single virus, as far as known, similar results would be obtained with the same type of tests but substituting other similarly available virus populations and complementary receptor cells, normal serum and anti-serum for the reagents used in the experiment.

The present invention is based on the discovery that a subpopulation having significantly increased cell receptor binding activity relative to the original viral population is obtained by complexing the virus with an inanimate substrate, preferably immobilized, or cells or cell derivatives, having sites which mimic cell receptor sites for the particular virus. A viral-cell complex is thus formed. (By the term "complex" as used herein is meant any linkage or binding to the substrate which holds the virus to the substrate through interaction of virus envelope cell binding site(s) with the receptor site(s) of the substrate during incubation and subsequent buffer washing. Covalent bonding, physical attraction, ionic bonding, etc., or combinations thereof could be involved.)

From the above, the inanimate substrate is a protein or glycoprotein having appropriate receptor reactive residues which will complex with the virus, which protein or glycoprotein optionally is coupled to an insoluble carrier, either directly or through one or more spacer moieties. Receptor reactive residues are those residues which mimic host cell receptor sites. For example, in Sendai, such residues are sialic acid residues.

Similarly, receptor bearing cells, cell membranes, or cell parts, or chemically modified cells, cell membranes or cell parts which all have receptor sites for the cell binding protein of the virus can be employed in place of the inanimate protein substrate to effect the cell enrichment. The cell membranes and cell parts are described hereinafter as "cell derivatives".

The following example illustrates the enrichment of Sendai virus for host cell receptor sites.

EXAMPLE 2

Fetuin (Grand Island Biological Co.), a glycoprotein containing N-acetylneuraminic acid, was immobilized on an arylamine controlled-pore glass using conventional activation and coupling procedures in a ratio of 25 mg fetuin per 100 mg glass. The immobilized fetuin was suspended in phosphate-buffered saline at 20 mg glass/ml and for binding studies ½ ml of this suspension, in order to remove any loosely attached protein, was incubated in RPMI 1640 medium containing 0.5% BSA at 37° C. for 30 minutes and then washed in 2 ml of the same buffer. About 0.5 ml of the UV-inactivated virus (equivalent to about 5,000 to 15,000 hemagglutination units of virus activity) was added to the immobilized fetuin and incubated at 4° C. in the RMPI 1640 (1.5% BSA) medium for 45 minutes. Thereafter, the glass-fetuin-virus complex was washed in cold (4° C.) RPMI medium (not containing BSA) and then resuspended in a small volume of the same medium. Temperature was elevated to 37° C. and maintained for 30 minutes. After centrifugation, the supernatant fluid containing the purified virus was stored at 4° C.

A radioligand using the purified virus was prepared with $I^{125}$ by standard chloramine-T procedure (see Hunter et al., *Nature*, 194, 495 (1962)). Again, unreacted $I^{125}$ was removed as previously described. The iodinated virus can be stored at 4° C. and rechromatographed on Sepharose 4B prior to use.

Using procedures substantially as described in Example 1, but substituting the fetuin receptor purified virus, the following results were obtained (Table II).

TABLE II

BINDING OF IODINATED RECEPTOR-PURIFIED SENDAI VIRUS TO CELLS AND IMMOBILIZED ANTIBODY

| SAMPLE | AMOUNT | % TOTAL COUNTS LIGAND BOUND AT 4° C. AND 25° AFTER A 2-HOUR INCUBATION | |
|---|---|---|---|
| | | 4° | 25 |
| Blank | | 21 | 17.1 |

TABLE II-continued
BINDING OF IODINATED RECEPTOR-PURIFIED SENDAI VIRUS TO CELLS AND IMMOBILIZED ANTIBODY

| SAMPLE | AMOUNT | % TOTAL COUNTS LIGAND BOUND AT 4° C. AND 25° AFTER A 2-HOUR INCUBATION | |
|---|---|---|---|
| | | 4° | 25 |
| HRBC | $1 \times 10^8$ cells | 22 | 20.1 |
| SRBC | $8 \times 10^7$ cells | 49.1 | 50.1 |
| SRBC | $1.7 \times 10^7$ cells | 30.3 | 36.6 |
| CCL-119 | $1.1 \times 10^6$ cells | 28.0 | 32.7 |
| NGS-IMA* | 0.2 mg glass | 19.9 | 22.9 |
| SV-IMA* | 0.2 mg glass | 88.5 | 86.6 |
| TCA precipitable counts | | 91 | — |

Abbreviations:
SRBC, CCl-119, as in Table I
HRBC - horse red blood cells
NGS-IMA - immobilized normal goat serum*
SV-IMA - immobilized goat antibody to Sendai Virus*; antibody was obtained from Microbiological Associates, Walkersville, MD.
TCA - Trichloracetic acid - indicates maximum amount of radiolabel that can be precipitated.
*Immobilized on the same controlled pore glass as used previously.

To confirm that the cell binding of Sendai virus occurs predominantly through sialic acid receptors, SRBC were treated with neuraminidase and then contacting with the receptor-purified Sendai virus. The total count bound dropped to about the blank reading.

EXAMPLE 3

This example was designed to examine the specificity of the virus-cell binding reaction using the receptor-purified Sendai virus. In these specificity studies, the procedures described with reference to Examples 1 and 2 hereinbefore were essentially followed except for mixing of the potential inhibitor with the cells or IMA prior to the addition of ligand. The percent displacement (% D) was calculated using the formula:

$$\% D = \frac{B_o - B}{B_o} \times 100$$

wherein B represents the counts bound with inhibitor, and $B_o$ represents the counts bound without inhibitor, both values being corrected for a blank reading.

TABLE III
DISPLACEMENT OF IODINATED SENDAI VIRUS BINDING AT 20° C.

| | % Displacement From | |
|---|---|---|
| Inhibitor[a] (amount) | SV-IMA[b] | SRBC[c] |
| T-1 Coliphage (57 μg) | 1.8 | <1.0 |
| Murine Leukemia Virus (12.9 μg) | <1.0 | <1.0 |
| Sendai Virus (13.7 μg) | 58.7 | 24.0 |
| Sendai Virus (27.4 μg) | 67.1 | 40.2 |
| Normal Goat Serum (0.4 μl) | <1.0 | 1.0 |
| Sendai Virus Antiserum (0.4 μl) | 14.3 | 54.1 |

[a]T-2 Coliphage - *Escherichia coli* bacteriophage obtained Miles Laboratories, Inc., Elkhart, IN.
Murine Leukemia Virus, Rauscher Strain, obtained from Bionetics Laboratory Products, Kensington, MD.
Sendai Virus - UV-inactivated obtained from Microbiological Associates, Walkersville, MD.
Sendai Virus Antiserum prepared in goats was obtained from Microbiological Associates, Walkersville, MD.
[b]SV-IMA, immobilized goat antiserum to Sendai Virus, 0.2 mg glass, $B_o$CPM corrected, 29,506.
[c]SRBC, sheep red blood cells, $8 \times 10^7$ cells, $B_o$CPM corrected, 14,025.

Table III shows the results of competitive inhibition experiments designed to examine the specificity of the virus-cell binding reaction. Binding of the labeled virus to immobilized antibody or to sheep red blood cells was significantly inhibited by cold Sendai virus or antibody to the virus but not by Murine leukemia virus, T-2 coliphage or normal goat serum.

The virus population enriched for host cell receptor binding has a gel profile different from biochemically purified virus. It is theorized that this difference (which involves changes in proportional amounts of viral envelope protein found) may at least partially explain the increase in cell receptor sensitivity.

EXAMPLE 4

Gel Analysis Of Sendai Virus Radioligand

Figure 2:
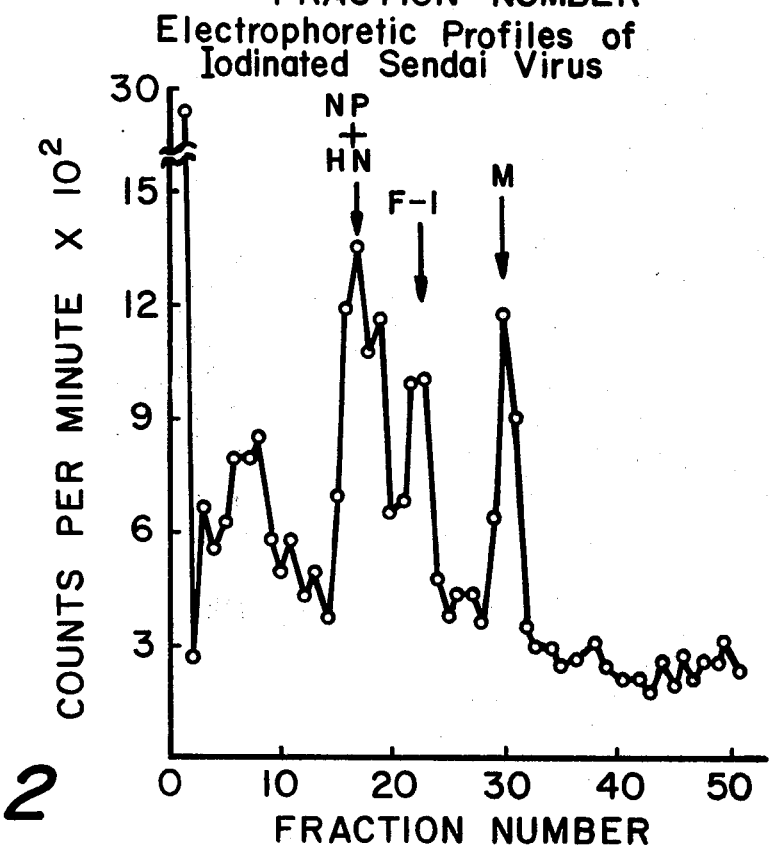

Sendai virus was purified biochemically (pellitization at 37,000×RCF for 75 minutes, and/or via Sepharose 4B chromatography) and by adsorption and elution from immobilized fetuin. The two preparations were iodinated and examined by polyacrylamide gel electrophoresis in 0.1% sodium dodecyl sulfate solution (FIGS. 1 and 2, respectively); see Maizel, J. V., Jr. in *Methods in Virology*, edited by K. Moramorosch and H. Koprowski, Vol. 5, pp. 179–246, Academic Press, Inc. N.Y., 1971. Acrylamide concentration was 7.5% and after electrophoresis, the gels were stained, destained, frozen, sliced, and each fraction was counted for radioactivity. The Figures of the drawings show the results. Both preparations contain the three major membrane proteins designated by convention (Scheid, A. and Choppin, P. W., *Virology*, 57, 470–495, (1974)) as membrane protein (M, 38,000 MW), fusion factor (F-1, 51,000 MW), and hemagglutinin-neuraminidase (HN, 68,000 MW). However, the gels differ in two major points: (1) the HN protein is substantially more prominent in the receptor-purified preparation; and (2) the high molecular weight areas of the gel (fractions 1 through 10) contain much more protein relative to the other peaks in the biochemically purified preparation than in the receptor-purified preparation.

Although gel profiles can vary due to exact electrophoretic conditions, sample labeling, and degree of purification of the virus, these results show that radioviral ligand obtained through a receptor purification step is complex and is composed of the envelope proteins indicative of those expected to be found in Sendai virus. In addition, the gel profiles in the drawings suggest that a Sendai virus radioligand which effectively binds cells would exhibit a gel profile with a prominent HN peak and less protein relative to the other peaks in the high molecular weight gel area.

Returning to a more general description of the invention, it is believed that the principles demonstrated in the aforegoing examples are applicable to many different types of virus, once a virus-host cell complexation mechanism is known. Then an inanimate substrate, cell or cell derivative to mimic a host cell binding moiety is selected to prepare the enriched virus population, for example, with immobilized concanavalin A, Bovine Leukemia Virus or Murine Leukemia Virus might be complexed and released. In a similar manner, even with the viruses which are known to bind to receptor cells through sialic acid groups, which include influenza viruses and paramyxoviruses, the particular substrate used for the enrichment procedure need not be fetuin. Essentially any sialic acid-containing protein, conjugate, hapten, analog, etc., such as bovine submaxillary mucin and N-acetylneuramin lactose, could be employed to effect the virus enrichment in such a case. Although for various reasons a theoretically usable inanimate substrate, cell or cell derivative may be inoperable, routine experimentation by the skilled artisan using a labeling technique can determine usefulness of a particular substrate. It is preferred that the substrate be immobilized as disclosed hereinbefore, but the exemplified controlled-pore glass need not be used. For example, Sepharose, acrylamide or plastic can be used to immobilize the complementary site-containing material.

EXAMPLE 5

One variation of this invention is the use of receptor bearing cells to effect the enrichment. Table IV shows the results when Sendai virus, purified by adsorption and elution from CCl-119 cells is iodinated and reacted with cells and immobilized antibody—the binding quality of the ligand is similar to that demonstrated in Table II which employed a ligand previously enriched using immobilized fetuin. The cytopurification procedure can be effected with any receptor-containing cell, cell membrane, or cell part, or chemically modified cell, cell membrane or cell part, which contains the appropriate active receptors. The exact complexation and release steps will vary for different systems but could be arrived at by those skilled in the art. The cytopurification procedure would be an important step in preparing enriched populations of viral ligands to those viruses to which the chemical nature of the receptor is unknown and for those viruses for which the preparation of an inanimate substrate is not possible.

TABLE IV

BINDING OF IODINATED CYTOPURIFIED SENDAI VIRUS TO CELLS AND IMMOBILIZED ANTIBODY

| SAMPLE | AMOUNT | % TOTAL COUNTS BOUND AT 4° C. AFTER A 1-HOUR INCUBATION |
|---|---|---|
| Blank | — | 7.3 |
| HRBC | $1.5 \times 10^8$ | 7.9 |
| SRBC | $1.5 \times 10^8$ | 42.2 |
| CCl-119 | $1.7 \times 10^7$ | 33.4 |
| SV-IMA | 2 mg glass | 57.4 |
| NGS-IMA | 2 mg glass | 17.9 |
| TCA Precipitable counts | | 63.5 |

Abbreviations as in Table II

The particular means used to release the enriched virus population from the substrate will vary according to the complexation mechanism. More than one technique could be considered for a particular complex. For example, even with the Sendai virus-sialic acid protein receptor complex, instead of temperature change, elution via competitive sialic acid-containing materials (hapten, derivative, or even analog) could be considered. Other routine procedures used in immunoassay procedures, i.e., pH, use of dissociating agents, such as high salt or ion concentrations or the like, and combinations thereof, could be considered.

The enriched virus ligand need not be radioactive but could be marked in other known manners, such as through enzyme labeling and fluorescent labeling. Of course, where a radioactive tracer is used, it need not be $I^{125}$.

The labeled virus ligand can be employed in any type of competitive binding procedure where the whole virus ligand could be used, such as an antigen in immunoassay procedures. Quantitative procedures for receptor positive cells, tissues, glycoproteins, body fluids, body exudate, etc. or antigen binding studies can be carried out. For example, the radiolabeled Sendai virus could be used to quantitate appropriate sialic acid receptors, differentiate between glycolylneuraminic acid- and acetylneuraminic acid-containing proteins, and so on.

Variations of the invention will be apparent to the skilled artisan.

What is claimed is:

1. A method for preparing a virus subpopulation characterized by significantly increased binding sensitivity toward host cells for the virus, which method comprises contacting a virus population with an inanimate substrate having moieties which mimic host cell receptor sites for cell binding protein of the virus, complexing at least a portion of the virus population with the substrate, removing non-complexed virus, dissociating the complex and recovering the complexed virus from the substrate as said subpopulation.

2. The method of claim 1 wherein the substrate is immobilized.

3. The method of claim 2 wherein the virus and the substrate complex through sialic acid moieties of the substrate.

4. The method of claim 3 wherein the virus is an influenza virus or paramyxovirus.

5. The method of claim 4 wherein the virus is Sendai virus.

6. The method of claim 5 wherein the substrate is a protein or glycoprotein.

7. The method of claim 4 wherein the complex is dissociated by change in temperature.

8. The method of claim 5 wherein the complex is dissociated by change in temperature.

9. The biologically pure virus subpopulation prepared by the process of claim 1.

10. The biologically pure virus subpopulation prepared by the process of claim 4.

11. The biologically pure virus subpopulation prepared by the process of claim 6.

12. A method for preparing a labeled virus subpopulation characterized by significantly increased binding sensitivity toward host cells for the virus, which method comprises contacting a virus population with an inanimate substrate having moieties which mimic host cell receptor sites for cell binding protein of the virus, complexing at least a portion of the virus population with the substrate, removing non-complexed virus from the substrate as a subpopulation and labeling the subpopulation.

13. The method of claim 12 wherein the substrate is immobilized.

14. The method of claim 13 wherein the virus and the substrate complex through sialic acid moieties of the substrate.

15. The method of claim 14 wherein the virus is an influenza virus or paramyxovirus.

16. The method of claim 15 wherein the virus is Sendai virus.

17. The method of claim 16 wherein the substrate is a protein or glycoprotein.

18. The method of claim 15 wherein the complex is dissociated by change in temperature.

19. The method of claim 16 wherein the complex is dissociated by change in temperature.

20. The method of claim 12 wherein the label is radioactive, enzyme or fluorescent.

21. The method of claim 15 wherein the label is radioactive, enzyme or fluorescent.

22. The method of claim 16 wherein the label is radioactive, enzyme or fluorescent.

23. The biologically pure labeled virus subpopulation prepared by the process of claim 20.

24. The biologically pure labeled virus subpopulation prepared by the process of claim 21.

25. The biologically pure labeled virus subpopulation prepared by the process of claim 22.

26. In a biological complementary binding procedure wherein a whole cell virus is complexed with a complementary substrate, the improvement which comprises using the virus subpopulation of claim 9 as said whole cell virus.

27. The process of claim 26 wherein the substrate is cells, tissues, glycoproteins, body fluid or body exudate.

28. A method for preparing a labeled virus subpopulation characterized by significantly increased binding sensitivity toward host cells for the virus, which method comprises contacting a virus population with cells, cell membranes, or cell parts or chemically modified cells, cell membranes or cell parts which have cell receptor sites for the cell binding protein of the virus, complexing at least a portion of the virus population with the cell, cell membrane or cell part or chemically modified derivative thereof, removing non-complexed virus, dissociating the complex and recovering the complexed virus from the cell or cell derivative as a subpopulation and labeling the subpopulation.

29. The method of claim 28 wherein the cell, cell membrane or cell part or chemical modification of the same is free or immobilized.

30. The method of claim 29 wherein the virus and the cell, cell membrane, or cell part or a chemically modified derivative of the same complex through sialic acid moieties of the cell, cell membrane, cell part or chemically modified derivative thereof.

31. The method of claim 30 wherein the virus is an influenza virus or paramyxovirus.

32. The method of claim 31 wherein the virus is Sendai virus.

33. The method of claim 31 wherein the complex is dissociated by change in temperature.

34. The method of claim 32 wherein the complex is dissociated by change in temperature.

35. In a qualitative or quantitive competitive binding assay process wherein a radioactive labeled, enzyme labeled or fluorescent labeled influenza virus or paramyxovirus is used, the improvement which comprises using the radioactive labeled, enzyme labeled or fluorescent labeled virus subpopulation of claim 23 as said labeled virus.

36. The process of claim 35 wherein the labeled virus subpopulation is radiolabeled Sendai virus.

37. The process of claim 36 wherein the labeled virus subpopulation is used as an antigen in a radioimmunoassay.

38. The process of claim 36 wherein the labeled virus subpopulation is used in an antibody binding study.

39. The process of claim 36 wherein the labeled virus subpopulation is used to quantitate sialic acid-containing protein in a radioimmunoassay.

40. The process of claim 36 wherein the labeled virus subpopulation is used to quantitate Sendai virus or Sendai virus protein.

41. The process of claim 36 wherein the labeled virus subpopulation is used as a radioligand to detect and/or quantitate cells, tissues, glycoproteins or body fluids or exudates which contain various sialic acid receptors, including acetylneuraminic acid.

42. The process of claim 36 wherein the labeled virus is used to differentiate between glycolylneuraminic acid-containing proteins and acetylneuraminic acid-containing proteins.

* * * * *